(12) United States Patent
Clarke et al.

(10) Patent No.: US 8,297,439 B2
(45) Date of Patent: Oct. 30, 2012

(54) PACKAGING FOR A STENT DELIVERY SYSTEM

(75) Inventors: Frank Clarke, Galway (IE); Thomas Farrell, Galway (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 120 days.

(21) Appl. No.: 12/796,285

(22) Filed: Jun. 8, 2010

(65) Prior Publication Data
US 2010/0264050 A1 Oct. 21, 2010

Related U.S. Application Data

(62) Division of application No. 10/543,477, filed as application No. PCT/IE03/00013 on Jan. 27, 2003, now Pat. No. 7,762,044.

(51) Int. Cl.
*A61B 17/06* (2006.01)

(52) U.S. Cl. .................... 206/204; 206/439; 206/484

(58) Field of Classification Search ............. 206/438, 206/439, 440, 363, 370, 204, 524.1, 524.2, 206/524.3, 524.4, 524.6, 484, 484.1, 484.2
See application file for complete search history.

(56) References Cited

U.S. PATENT DOCUMENTS

| | | | |
|---|---|---|---|
| 3,815,315 A | 6/1974 | Glick | |
| 3,939,971 A | 2/1976 | Tulis | |
| 4,179,338 A | 12/1979 | Gordon | |
| 4,616,046 A | 10/1986 | Kornbaum et al. | |
| 4,660,721 A | 4/1987 | Mykleby | |
| 4,778,656 A | 10/1988 | Allen et al. | |
| 4,813,210 A | 3/1989 | Fukui et al. | |
| 4,987,997 A * | 1/1991 | Raszewski et al. | 206/720 |
| 5,014,494 A | 5/1991 | George | |
| 5,137,688 A | 8/1992 | DeRudder | |
| 5,342,673 A * | 8/1994 | Bowman et al. | 428/198 |
| 5,385,229 A * | 1/1995 | Bittmann et al. | 206/210 |
| 5,417,969 A | 5/1995 | Hsu et al. | |
| 5,431,970 A * | 7/1995 | Broun et al. | 428/36.5 |
| 5,551,781 A * | 9/1996 | Wilkes et al. | 383/205 |
| 5,554,120 A | 9/1996 | Chen et al. | |
| 5,577,368 A | 11/1996 | Hamilton et al. | |
| 5,590,778 A * | 1/1997 | Dutchik | 206/439 |
| 5,715,943 A * | 2/1998 | Thompson, Jr. | 206/363 |
| 5,800,542 A | 9/1998 | Li | |
| 5,816,403 A * | 10/1998 | Wilkes et al. | 206/438 |
| RE36,132 E | 3/1999 | Heacox | |
| 5,881,534 A | 3/1999 | Ahlqvist et al. | |
| 6,065,597 A | 5/2000 | Pettersson et al. | |
| 6,251,489 B1 * | 6/2001 | Weiss et al. | 428/35.2 |
| 6,349,822 B1 * | 2/2002 | Greene | 206/308.1 |
| 6,461,630 B1 | 10/2002 | Tucker et al. | |
| 6,520,323 B1 | 2/2003 | Colombo | |
| 6,889,839 B1 | 5/2005 | Rosten et al. | |
| 7,631,760 B2 * | 12/2009 | Guelzow et al. | 206/438 |
| 2003/0083616 A1 | 5/2003 | Lee et al. | |
| 2003/0168370 A1 | 9/2003 | Merboth et al. | |
| 2004/0101958 A1 | 5/2004 | Shimp | |
| 2004/0200754 A1 | 10/2004 | Hagemeier | |
| 2005/0194723 A1 | 9/2005 | Muratoglu et al. | |
| 2006/0260967 A1 | 11/2006 | Clarke et al. | |
| 2011/0079525 A1 * | 4/2011 | Peck et al. | 206/438 |

\* cited by examiner

*Primary Examiner* — Jacob K Ackun

(57) ABSTRACT

The present invention relates to a method of packaging and a packaging system for treated stents which minimize the level of exposure of the stents to oxygen, moisture and light. The package comprises two compartments, the compartments being in communication with each other via a breathable membrane.

4 Claims, 4 Drawing Sheets

PACKAGING FOR A STENT DELIVERY SYSTEM

CROSS-REFERENCE TO RELATED APPLICATIONS

This application is a division of patent application Ser. No. 10/543,477, which is the U.S. National Stage of International Application No. PCT/IE03/00013, filed Jan. 27, 2003.

FIELD OF THE INVENTION

The present invention relates to a method of packaging and a packaging system for stent delivery systems which minimise the level of exposure of the stents to oxygen, moisture and light.

BACKGROUND TO THE INVENTION

Cardiovascular disease, including atherosclerosis, is the leading cause of death in the U.S. A number of methods and devices for treating coronary heart disease have been developed, some of which are specifically designed to treat the complications resulting from atherosclerosis and other forms of coronary arterial narrowing.

One method for treating atherosclerosis and other forms of coronary narrowing is percutaneous transluminal coronary angioplasty, hereinafter referred to as "angioplasty" or "PTCA". The objective in angioplasty is to enlarge the lumen of the affected coronary artery by radial expansion. This is generally accomplished by inflating a balloon within the narrowed lumen of the affected artery. The wall of the artery itself may also be stretched as the balloon is inflated. With simple angioplasty, the balloon is threaded through the artery with a catheter and inflated at the place where the blood vessel is blocked. After the procedure, the balloon is then removed. With simply angioplasty alone, arteries may close up again or re-narrow. This narrowing is known as restenosis.

To reduce the risk of restenosis, a stent may also be inserted during angioplasty. A stent is a tube, often made of metals or occasionally plastic materials that is inserted into a vessel or a passage in the body to keep the lumen of the vessel open and to prevent closure due to a stricture or external compression. The use of a stent may reduce the risk of restenosis. However, stent insertion can cause undesirable reactions such as inflammation, infection, thrombosis, or proliferation of cell growth that occludes the passageway.

Restenosis occurs because the blood vessel wall is injured when the stent is implanted. The area then becomes inflated and new cells form scar tissue. The arterial walls may become so thick in some instances that they sometimes protrude into the mesh of the stent. In such cases, a further angioplasty may be undergone, and a new stent may be placed inside the existing one. If restenosis continues, the eventual alternative may be bypass surgery.

Alternatively, a treated stent may be inserted during the angioplasty. Such a treated stent may eliminate the need for repeat angioplasties and could spare some patients the trauma, risk and prolonged recovery associated with heart bypass surgery. The treated stent contains a therapeutic agent to assist in preventing restenosis. The stent is bioengineered to release doses of the therapeutic agent which may or may not be contained in a coating on the stent. Agents contemplated act to stop new cells from forming without impairing the healing of the vessel. Agents may also dampen inflammation and have antibiotic properties.

However, because the treated stent may contain a therapeutic drug, treated stents present problems associated with drug administration. For example, for a drug to be administered effectively, the integrity of the drug's effective dosage should be maintained. Certain drugs require regulated conditions for efficacy, such as regulated air circulation or lack thereof, regulated exposure to light and oxygen.

Prior art packaging systems for treated stents have typically comprised a thermoform tray insert in a foil pouch, or a thermoform tray having a TYVEK® material lid in a foil pouch, into which the stent is vacuum packed. Such conventional packaging for stents do not provide for regulation of ambient conditions such as circulation of air or exposure to light and oxygen. Without such appropriate regulation, the efficacy of the drug and/or drug coating may be reduced. Moreover, these packages tend to be heavier than those of the present invention, they utilise more material and they require more operator handling time to pack and so are more labour intensive to produce. TYVEK® material is commercially available from DuPont and consists of multiple spun woven extruded polyethylene strands, compressed under high pressure to form a complex system of microscopic porous channels which provides a tortuous path within a thin flexible opaque sheet.

OBJECT OF THE INVENTION

It is thus an object of the present invention to provide a process for packaging stents which is simple to operate, and which produces a package which optimises ambient conditions for treated stents. It is also an object to provide a package for treated stents and their associated delivery systems, which provides a barrier to oxygen, moisture and light. It is a further object of the invention that the packaging maintains a level of environmental control within the sterile barrier. This will be achieved by the inclusion of oxygen and moisture absorbing agents within the sealed package. The package must also be suitable for sterilisation by both ethylene oxide (EtO) and gamma radiation.

SUMMARY OF THE INVENTION

According to the present invention there is provided a process for packaging a treated stent comprising;
  (a) placing the treated stent within one compartment of a package which comprises two compartments, the compartments being in communication with each other via a breathable membrane;
  (b) sealing at least the compartment containing the stent; and
  (c) sterilising the package.

Suitably the package comprises at least one outer wall and an inner wall, the inner wall being formed from the breathable membrane.

The breathable membrane suitably provides a barrier to microbes but allows the passage of air and other gases and moisture. One suitable material is TYVEK® material, and another is paper.

In one embodiment the package comprises two outer walls and one internal wall. The outer walls may be made of a plastics-coated foil and the internal wall may be made of the breathable membrane. The outer walls may further comprise an outer layer of a peelable material. The internal wall may be attached to one outer wall adjacent its outer edge, to form a pocket open at one end. Suitably, the internal wall is smaller than the outer wall so that one compartment is smaller than the other. This has the advantage that the package uses as little breathable membrane as possible.

In this embodiment, before sealing the compartment, the following additional steps are performed;—
- (d) placing at least one moisture or oxygen scavenger pack in the second of the two compartments;
- (e) flushing the package with an inert gas; and
- (f) applying a vacuum to the package.

In this embodiment both compartments may be sealed in a single operation. The sealed package may then be sterilised by gamma radiation in a conventional manner.

In another embodiment one outer wall may comprise foil over only a portion of its surface such that an area of the breathable membrane is exposed. This embodiment is suitable for sterilisation of the contents by ethylene oxide gas since the exposed membrane provides an entry and exit for the sterilant gas. In this embodiment the stent is sealed in the compartment and then the package is sterilised with ethylene oxide. Following sterilisation, at least one moisture or oxygen scavenger pack is placed in the second of the two compartments. The package is then flushed with an inert gas and a vacuum is applied to the package. Following vacuum draw down the package is sealed across all three layers of the pouch to seal the second compartment closed. Excess pouch material, between the first and second seals may then be cut away.

One compartment of the package is thus adapted to hold an oxygen absorber pack or a moisture absorber pack or both. In the second embodiment the scavenger packs are not placed in the package until after ethylene oxide sterilisation to prevent the absorber packs being saturated by the sterilisation process.

One corner of the package, remote from the sealed end is provided with a peel seal which allows the package to be opened. By providing the peel seal at a position remote from the edge which seals the package closed, the package can be torn open to remove the stent without breaching the absorber pack compartment.

The edges of the package which are to be sealed together may be coated with an easy peel adhesive, which would show a mark on opening if the seal had not been intact in any given area.

The inert gas used to flush the package is preferably nitrogen. The package may be sealed by clamping the edges of the package between upper and lower jaws of a sealing device.

The package is particularly adapted to house a stent and its associated delivery systems, but would also be suitable for use in any application where moisture, oxygen and/or light exposure must be minimised. The provision of two compartments allows interaction of the scavenger packs with the treated stent, but without any physical contact.

BRIEF DESCRIPTION OF THE DRAWINGS

The invention will now be described in greater detail with reference to the accompanying drawings in which.

DETAILED DESCRIPTION OF THE DRAWINGS

Figure 1:
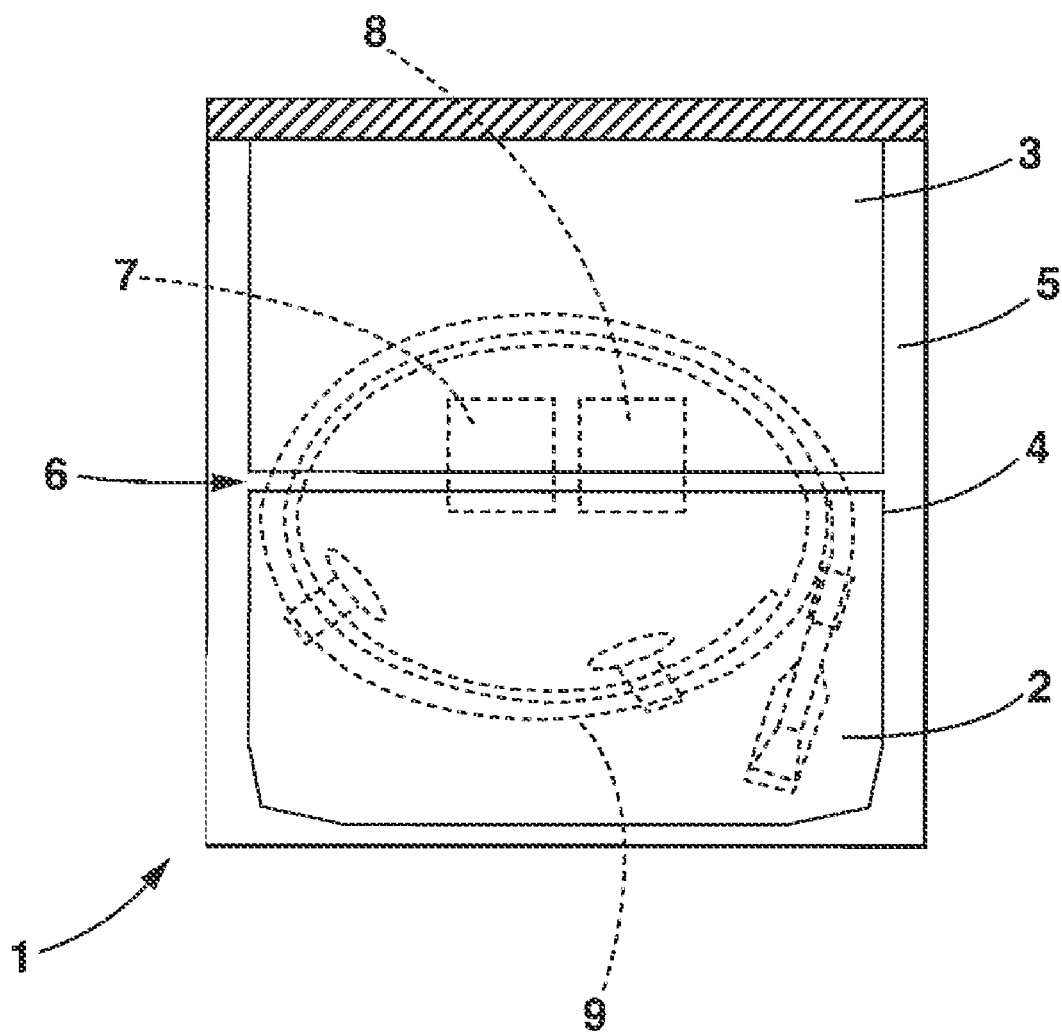
FIG. 1 shows a first package configuration in accordance with the invention, suitable for sterilisation with gamma radiation, with the treated stent and absorber packs in place.

The packaging for a treated stent delivery system takes the form of a pouch or bag (1), as shown in FIG. 1. The pouch (1) is provided with two compartments (2, 3). The compartments are formed by sealing a sheet of breathable membrane (4) such as TYVEK® material, to a layer of laminated foil (5) and then sealing the two layers of laminated foil (5) together. The sheet (4) is shorter than layers (5) but of the same width, so that the sheet (4) is sealed along the line (6) and its side edges to layer (5). This means that the two compartments are of different sizes and is less wasteful of materials.

Besides TYVEK® material, other breathable membranes, such as paper, that suitably provide a barrier to microbes but allow the passage of air and other gases and moisture could also be used. TYVEK® material has the advantage of having greater tear strength than paper and so is less likely to tear on application of the vacuum.

One compartment (2) is adapted to contain oxygen and moisture absorber packs (7, 8). Suitable oxygen and moisture absorber packs are commercially available from Mitsubishi Gas chemical company, Inc./(PHARMAKEEP KD-20™), and Silgel Ltd./(4 g Molecular Sieve sachets), respectively. The other compartment (3) is adapted to contain the treated stent (9). This compartment is larger than compartment (2). Forming the compartments with one wall made of TYVEK® material allows the absorber packs (7, 8) to interact with the coated stent delivery system (9) but at the same time prevents direct contact between the absorber packs and the delivery system. The advantage of not putting the moisture absorber packs into direct contact with the delivery system is that there is a possibility that tiny amounts of content residue would be present on the outside of each pack, and this residue would adversely interact with the drug coating.

EXAMPLE 1

The process for packaging a stent which is sterilised by gamma radiation comprises placing a coated stent, mounted on a delivery system and loaded into a coiled dispenser, into the larger of the two compartments of the pouch. In this embodiment the compartment is 280 mm long and 250 mm wide. The layer of TYVEK® material is located between two layers of foil, which are both of equal length, so that no portion of the TYVEK® material is exposed.

The moisture and oxygen absorber packs are placed in the second compartment which is 120 mm long. The TYVEK® material layer thus separates the scavenger packs from the stent but allows interaction between the two compartments.

In a single operation the open end of the pouch is flushed with nitrogen and vacuum-sealed, so that the two compartments are sealed together. Any excess material above the seal area is trimmed away, which eliminates the possibility of opening the pouch at this end.

The inert gas used to flush the package is preferably nitrogen. The nitrogen is flushed for between 1 and 10 seconds at a pressure of 10 to 30 psi. The vacuum draw down time is suitably 1 second, up to 10 seconds. The package may be sealed by clamping the edges of the package between upper and lower jaws of a sealing device. The seal time may be from 1 to 10 seconds, with an upper jaw seal temperature of 110 to 200° C. and a lower jaw seal temperature of 60 to 100° C. and the seal pressure may be from 30 to 100 psi.

The sealed pouch is then sterilised by gamma radiation in a conventional manner.

EXAMPLE 2

Figure 2:
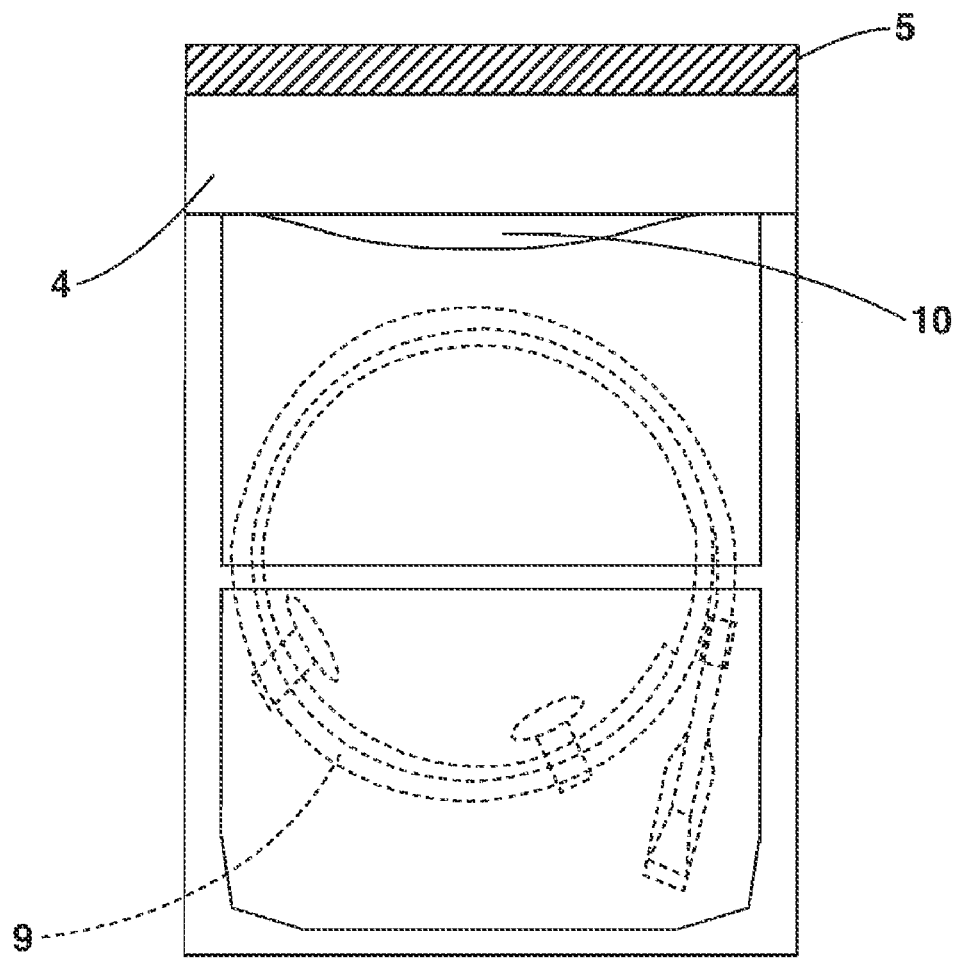
FIG. 2 shows an alternative package configuration in accordance with the invention, suitable for sterilisation with ethylene oxide, with the treated stent sealed in one compartment.
Figure 3:
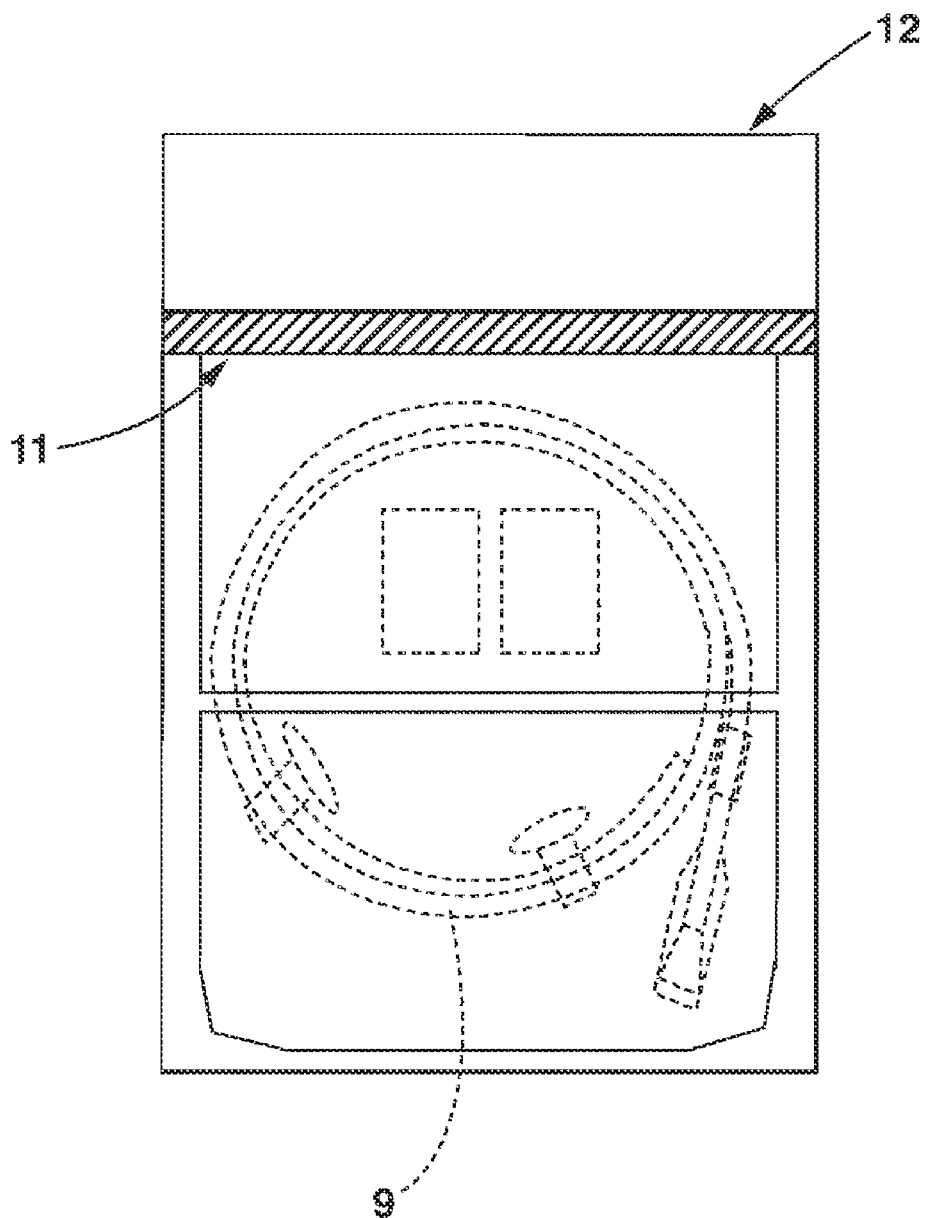
FIG. 3 shows the embodiment of FIG. 2 with the treated stent and absorber packs in place.

The process for packaging a stent which is sterilised by ethylene oxide is slightly different. As shown in FIGS. 2 and 3, the coated stent (9), mounted on a delivery system and loaded onto a coiled dispenser, is placed in the larger of the two compartments (3). In this embodiment the compartment (3) is 365 mm long. One of the two foil sheets (5) is shorter than the TYVEK® material layer (4) and the other foil sheet (5), so that a section of the TYVEK® material is exposed on the surface of the package (1). This exposed area (10) provides an entry and exit point for the ethylene oxide gas in the sterilisation process. The compartment (3) is then sealed at its open end, along the line (11) shown in FIG. 3, with a heated bar sealer as described in Example 1. Because one foil sheet (5) is shorter than the other it is not sealed in this operation and so one compartment (2) is left open at one end.

The package is then sterilised using ethylene oxide in a conventional manner.

Following sterilisation, oxygen and moisture absorber (7, 8) packs are placed in the smaller, unsealed compartment (2) of the pouch or package (1). This compartment is 145 mm long. The package (1) is then flushed with nitrogen and vacuum-sealed, as described above, across the opening of the scavenger pack compartment (2) along the line (12). Excess pouch material between the two seal lines (10) and (12) is then trimmed away, which eliminates the possibility of opening the pouch (1) at this end which could result in the scavenger packs being released and contaminating the stent.

Figure 4:
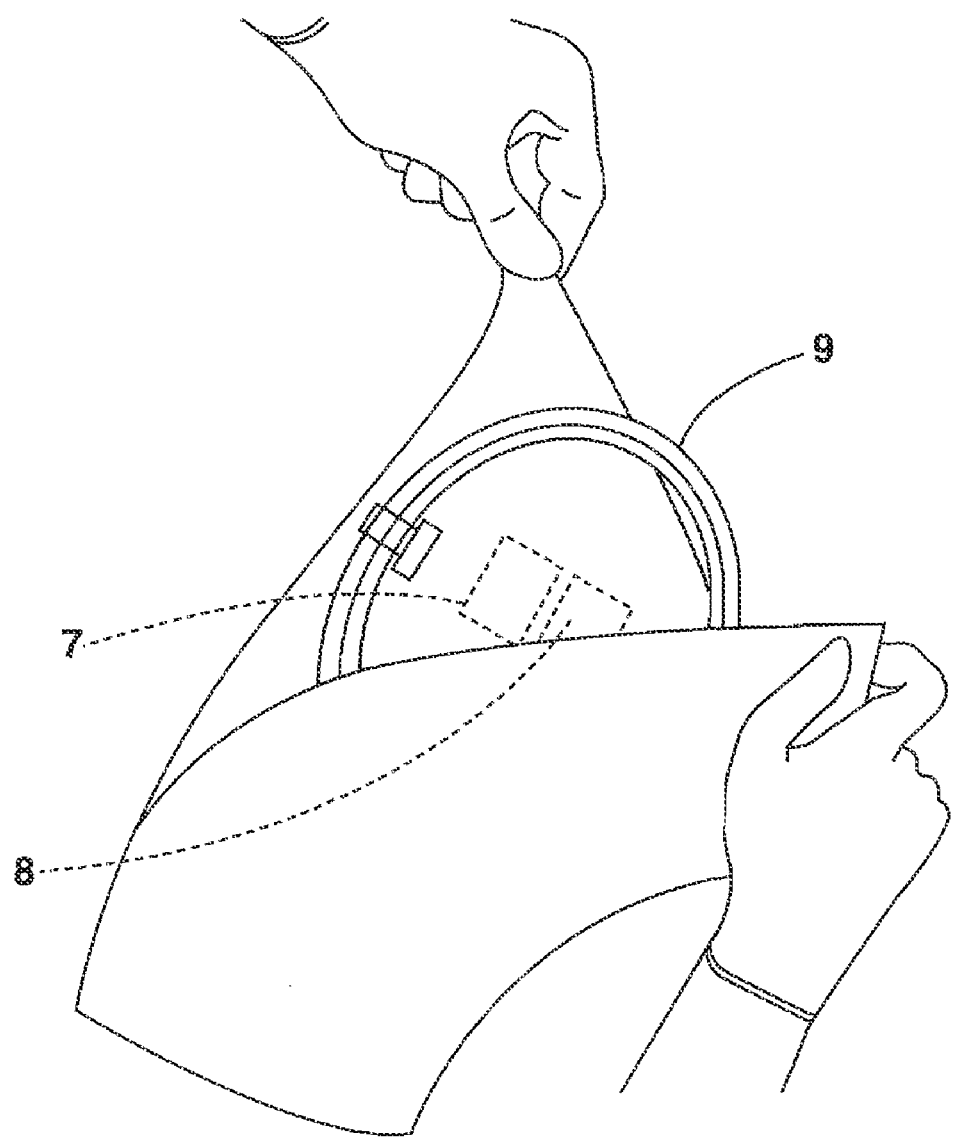
FIG. 4 shows a package being torn open to remove the treated stent.

FIG. 4 shows the package (1) being opened at one end to remove the stent, and the absorber packs (7, 8) being retained in compartment (2).

The words "comprises/comprising" and the words "having/including" when used herein with reference to the present invention are used to specify the presence of stated features, integers, steps or components but does not preclude the presence or addition of one or more other features, integers, steps, components or groups thereof.

The invention claimed is:

1. A packaged drug coated stent comprising:
   a pouch having:
      two outer walls of a plastics covered foil material; and
      an internal wall of a breathable membrane providing a barrier to microbes but allow the passage of air and other gases and moisture, the membrane being sealed to and extending over at least a portion of one of the outer walls to define first and second compartments within the pouch, with the compartments being in communication with each other only via the membrane;
   a drug coated stent disposed within the first compartment that is sealed such that the outer walls provide a barrier to oxygen, moisture and light; and
   one or more scavenger packs disposed within the second compartment, the one or more packs comprising an oxygen absorber pack and/or a moisture absorber pack.

2. The packaged drug coated stent of claim 1 wherein the drug coated stent and the interior of the first compartment are sterile.

3. The packaged drug coated stent of claim 1 wherein and the one or more scavenger packs and the interior of the second compartment are non-sterile.

4. The packaged drug coated stent of claim 1 wherein the first compartment is sealed such that the pouch can be peeled to open the first compartment without breaching the second compartment.

* * * * *